(12) United States Patent
Ciriello et al.

(10) Patent No.: US 12,029,619 B2
(45) Date of Patent: Jul. 9, 2024

(54) METHOD AND APPARATUS FOR CNA ANALYSIS OF TOOTH ANATOMY

(71) Applicant: Perceptive Technologies, Inc., Boston, MA (US)

(72) Inventors: Christopher John Ciriello, Boston, MA (US); Scott Howard Phillips, Victoria (CA)

(73) Assignee: Perceptive Technologies, Inc., Boston, MA (US)

( * ) Notice: Subject to any disclaimer, the term of this patent is extended or adjusted under 35 U.S.C. 154(b) by 0 days.

(21) Appl. No.: 18/177,691

(22) Filed: Mar. 2, 2023

(65) Prior Publication Data
US 2023/0200934 A1 Jun. 29, 2023

Related U.S. Application Data

(63) Continuation of application No. PCT/US2021/048893, filed on Sep. 2, 2021.

(60) Provisional application No. 63/074,400, filed on Sep. 3, 2020.

(51) Int. Cl.
*A61C 1/00* (2006.01)
*A61C 13/34* (2006.01)

(52) U.S. Cl.
CPC ............ *A61C 1/0015* (2013.01); *A61C 13/34* (2013.01)

(58) Field of Classification Search
CPC ....... A61C 1/0015; A61C 1/082; A61C 13/34; A61C 13/00004; A61H 20/40; A61B 17/1673; A61B 17/32002; A61B 17/320068
See application file for complete search history.

(56) References Cited

U.S. PATENT DOCUMENTS

| | | |
|---|---|---|
| 3,772,790 A | 11/1973 | Swan-Gett et al. |
| 4,941,826 A | 7/1990 | Loran et al. |
| 5,122,060 A | 6/1992 | Vassiliadis et al. |
| 5,343,391 A | 8/1994 | Mushabac |
| 5,516,286 A | 5/1996 | Kushner |
| 5,888,065 A | 3/1999 | Sussman |
| 6,049,743 A | 4/2000 | Baba |
| 6,518,033 B1 | 2/2003 | Gromeier et al. |
| 6,802,713 B1 | 10/2004 | Chishti et al. |

(Continued)

FOREIGN PATENT DOCUMENTS

| | | |
|---|---|---|
| CA | 2658807 A1 | 1/2008 |
| CN | 101883536 A | 11/2010 |

(Continued)

OTHER PUBLICATIONS

EP19800428.5 Extended European Search Report dated Feb. 22, 2022.

(Continued)

*Primary Examiner* — Cris L. Rodriguez
*Assistant Examiner* — Drew S Folgmann
(74) *Attorney, Agent, or Firm* — Wilson Sonsini Goodrich & Rosati (57) ABSTRACT

Provided herein are computer-implemented methods, computer-implemented systems, and a non-transitory computer-readable storage media for directing an automated dental drill (ADD) for preparation of a target tooth of a patient under the control of a practitioner.

20 Claims, 4 Drawing Sheets

(56) References Cited

U.S. PATENT DOCUMENTS

| | | |
|---|---|---|
| 6,845,190 B1 | 1/2005 | Smithwick et al. |
| 8,251,984 B2 | 8/2012 | Monty |
| 8,416,984 B2 | 4/2013 | Liang et al. |
| 8,716,973 B1 | 5/2014 | Lammertse |
| 9,408,673 B2 | 8/2016 | Monty |
| 9,554,872 B2 | 1/2017 | Koubi et al. |
| 9,622,833 B2 | 4/2017 | Monty |
| 9,675,419 B2 | 6/2017 | Akeel et al. |
| 9,788,915 B2 | 10/2017 | Monty et al. |
| 10,016,242 B2 | 7/2018 | Salcedo et al. |
| 10,568,499 B2 | 2/2020 | Tesar |
| 10,792,133 B2 | 10/2020 | Moon |
| 11,497,402 B2 | 11/2022 | Fan et al. |
| 2003/0135092 A1 | 7/2003 | Cline et al. |
| 2005/0047550 A1 | 3/2005 | Yao et al. |
| 2005/0177266 A1 | 8/2005 | Kopelman et al. |
| 2006/0127848 A1 | 6/2006 | Sogo et al. |
| 2006/0153254 A1 | 7/2006 | Franjic et al. |
| 2006/0166161 A1 | 7/2006 | Rose et al. |
| 2006/0177796 A9 | 8/2006 | Heasley |
| 2007/0115481 A1 | 5/2007 | Toth et al. |
| 2007/0265495 A1 | 11/2007 | Vayser |
| 2008/0009697 A1 | 1/2008 | Haider et al. |
| 2008/0096156 A1 | 4/2008 | Rose et al. |
| 2008/0153067 A1 | 6/2008 | Berckmans et al. |
| 2008/0276192 A1 | 11/2008 | Jones et al. |
| 2009/0142724 A1 | 6/2009 | Rosenblood et al. |
| 2009/0154768 A1 | 6/2009 | Bell |
| 2009/0186318 A1 | 7/2009 | Assa et al. |
| 2009/0187175 A1 | 7/2009 | Assa et al. |
| 2009/0248184 A1 | 10/2009 | Steingart et al. |
| 2009/0253095 A1 | 10/2009 | Salcedo et al. |
| 2010/0105011 A1 | 4/2010 | Karkar et al. |
| 2010/0291505 A1 | 11/2010 | Rawley et al. |
| 2011/0143306 A1 | 6/2011 | Hirsch et al. |
| 2011/0313825 A1 | 12/2011 | Wilhelm et al. |
| 2012/0059378 A1 | 3/2012 | Farrell |
| 2012/0113280 A1 | 5/2012 | Stupak et al. |
| 2012/0231421 A1 | 9/2012 | Boerjes et al. |
| 2013/0010079 A1 | 1/2013 | Zhang et al. |
| 2013/0021447 A1 | 1/2013 | Brisedoux et al. |
| 2013/0059264 A1 | 3/2013 | Monty |
| 2013/0188012 A1 | 7/2013 | Bellis et al. |
| 2013/0211242 A1 | 8/2013 | Bertrand et al. |
| 2013/0322719 A1 | 12/2013 | Dekel et al. |
| 2014/0107471 A1 | 4/2014 | Haider et al. |
| 2014/0272767 A1 | 9/2014 | Monty |
| 2014/0272773 A1 | 9/2014 | Merritt et al. |
| 2014/0272775 A1 | 9/2014 | Monty |
| 2015/0057576 A1 | 2/2015 | Chen |
| 2015/0057675 A1 | 2/2015 | Akeel et al. |
| 2015/0176775 A1 | 6/2015 | Gu et al. |
| 2015/0320320 A1 | 11/2015 | Kopelman et al. |
| 2015/0365604 A1 | 12/2015 | Griffith et al. |
| 2016/0012182 A1 | 1/2016 | Golay |
| 2016/0135816 A1 | 5/2016 | Lavallee et al. |
| 2016/0143703 A1 | 5/2016 | Monty et al. |
| 2016/0149369 A1 | 5/2016 | Monty et al. |
| 2016/0175076 A1 | 6/2016 | Hultgren et al. |
| 2016/0248994 A1 | 8/2016 | Liu |
| 2016/0331489 A1 | 11/2016 | Sanders et al. |
| 2016/0338803 A1 | 11/2016 | Pesach |
| 2016/0354169 A1 | 12/2016 | Suttin et al. |
| 2016/0367336 A1 | 12/2016 | Lv et al. |
| 2017/0020636 A1 | 1/2017 | Akeel et al. |
| 2017/0079746 A1 | 3/2017 | Sanders |
| 2017/0319277 A1 | 11/2017 | Cantor-Balan et al. |
| 2018/0078332 A1 | 3/2018 | Mozes et al. |
| 2018/0078335 A1 | 3/2018 | Falkel |
| 2018/0085203 A1 | 3/2018 | Ramirez et al. |
| 2018/0110589 A1 | 4/2018 | Gao |
| 2018/0325622 A1 | 11/2018 | Groves, Jr. et al. |
| 2019/0029524 A1 | 1/2019 | Kopelman et al. |
| 2019/0038367 A1 | 2/2019 | Ciriello et al. |
| 2019/0076026 A1 | 3/2019 | Elbaz et al. |
| 2019/0151042 A1 | 5/2019 | Holman et al. |
| 2019/0239969 A1 | 8/2019 | Abu-Akeel et al. |
| 2019/0298448 A1 | 10/2019 | Kerbage et al. |
| 2019/0336243 A1 | 11/2019 | Di Sessa et al. |
| 2019/0388194 A1 | 12/2019 | Atiya et al. |
| 2020/0000551 A1* | 1/2020 | Li .................. A61C 9/0053 |
| 2020/0163729 A1 | 5/2020 | Ciriello et al. |
| 2020/0178811 A1 | 6/2020 | Shindo |
| 2020/0315754 A1 | 10/2020 | Ciriello et al. |
| 2020/0390518 A1 | 12/2020 | Ciriello et al. |
| 2021/0169318 A1 | 6/2021 | Sorimoto et al. |
| 2021/0186667 A1 | 6/2021 | Abu-Tarif et al. |
| 2021/0205633 A1 | 7/2021 | Kerbage et al. |
| 2021/0228317 A1 | 7/2021 | Ciriello et al. |
| 2021/0251721 A1 | 8/2021 | Ciriello et al. |
| 2022/0183789 A1 | 6/2022 | Ciriello et al. |
| 2022/0354623 A1 | 11/2022 | Ciriello et al. |

FOREIGN PATENT DOCUMENTS

| | | |
|---|---|---|
| CN | 105832419 A | 8/2016 |
| CN | 107205795 A | 9/2017 |
| DE | 1032883 B | 6/1958 |
| DE | 10145104 A1 | 1/2003 |
| DE | 102005043402 A1 | 3/2007 |
| DE | 202010003663 U1 | 7/2010 |
| EP | 0553712 A1 | 8/1993 |
| EP | 2078493 A2 | 7/2009 |
| EP | 2459115 A2 | 6/2012 |
| EP | 2722003 A1 | 4/2014 |
| EP | 3037057 A1 | 6/2016 |
| EP | 3087948 A1 | 11/2016 |
| EP | 3288486 A1 | 3/2018 |
| EP | 3391810 A1 | 10/2018 |
| EP | 3476357 A1 | 5/2019 |
| FR | 2804859 A1 | 8/2001 |
| IN | 07/2016 | 2/2016 |
| JP | 2007244494 A | 9/2007 |
| KR | 20210122584 A | 10/2021 |
| RU | 2443396 C1 | 2/2012 |
| WO | WO-2004074324 A2 | 9/2004 |
| WO | WO-2006087445 A2 | 8/2006 |
| WO | WO-2007072866 A1 | 6/2007 |
| WO | WO-2007078512 A2 | 7/2007 |
| WO | WO-2011014802 A2 | 2/2011 |
| WO | WO-2011021192 A1 | 2/2011 |
| WO | WO-2012004018 A1 | 1/2012 |
| WO | WO-2012105972 A1 | 8/2012 |
| WO | WO-2013172919 A1 | 11/2013 |
| WO | WO-2014024157 A1 | 2/2014 |
| WO | WO-2014035010 A1 | 3/2014 |
| WO | WO-2015009856 A2 | 1/2015 |
| WO | WO-2015026546 A2 | 2/2015 |
| WO | WO-2015134633 A1 | 9/2015 |
| WO | WO-2015188286 A1 | 12/2015 |
| WO | WO-2016022347 A1 | 2/2016 |
| WO | WO-2016040657 A1 | 3/2016 |
| WO | WO-2016093984 A1 | 6/2016 |
| WO | WO-2016108276 A1 | 7/2016 |
| WO | WO-2016113745 A1 | 7/2016 |
| WO | WO-2016145093 A1 | 9/2016 |
| WO | WO-2016154589 A1 | 9/2016 |
| WO | WO-2016178212 A1 | 11/2016 |
| WO | WO-2017100828 A1 | 6/2017 |
| WO | WO-2017130060 A1 | 8/2017 |
| WO | WO-2018012862 A1 | 1/2018 |
| WO | WO-2018154485 A1 | 8/2018 |
| WO | WO-2018198095 A1 | 11/2018 |
| WO | WO-2019021718 A1 | 1/2019 |
| WO | WO-2019093426 A1 | 5/2019 |
| WO | WO-2019153413 A1 | 8/2019 |
| WO | WO-2019209637 A1 | 10/2019 |
| WO | WO-2019215511 A2 | 11/2019 |
| WO | WO-2019215512 A1 | 11/2019 |
| WO | WO-2021044218 A1 | 3/2021 |
| WO | WO-2021155045 A1 | 8/2021 |
| WO | WO-2021257708 A1 | 12/2021 |

(56) References Cited

FOREIGN PATENT DOCUMENTS

| WO | WO-2022051516 A1 | 3/2022 |
|----|------------------|--------|
| WO | WO-2022060800 A1 | 3/2022 |
| WO | WO-2022212507 A1 | 10/2022 |

OTHER PUBLICATIONS

European Patent Application No. 18757107.0 European Search Report dated Feb. 4, 2021.
Fried et al.: Ablation of Dental Hard Tissues with a Microsecond Pulsed Carbon Dioxide Laser Operating at 9.3-μm with an Integrated Scanner. Proc SPIE Int Soc Opt Eng. 6843:16 pages (2008).
Fried et al.: Frailty in older adults: evidence for a phenotype. J Gerontol A Biol Sci Med Sci.; 56(3):M146-56 (2001).
Geomagic Sculpt website http://www.geomagic.com/en/products/sculpt/touch/ (automatically redirected to https://www.3dsystems.com/software/geomagic-sculpt ), accessed Oct. 2, 2018.
Kauer et al.: Clinical evaluation of effects of low-level lasers on pain during cavity preparation. International Journal of Research—Granthaalayah. 6(10):81-86 (2018).
Kim et al.: Improved accuracy in periodontal pocket depth measurement using optical coherence tomography. J Periodontal Implant Sci. 47(1):13-19 (2017).
Le et al.: A non-invasive imaging and measurement using optical coherence tomography angiography for the assessment of gingiva: An in vivo study. J Biophotonics. 11(12) (2018).
PCT/IB2017/000109 International Preliminary Report on Patentability dated Jul. 31, 2018.
PCT/IB2017/000109 International Search Report and Written Opinion dated Jun. 14, 2017.
PCT/IB2018/051115 International Search Report and Written Opinion dated Jun. 5, 2018.
PCT/IB2019/000578 International Preliminary Report on Patentability dated Nov. 10, 2020.
PCT/IB2019/000578 International Search Report and Written Opinion dated Nov. 18, 2019.
PCT/IB2020/000729 International Preliminary Report on Patentability dated Mar. 8, 2022.
PCT/IB2020/000729 International Search Report and Written Opinion dated Dec. 31, 2020.
PCT/US2021/015555 International Search Report and Written Opinion dated Apr. 14, 2021.
PCT/US2021/037635 International Search Report and Written Opinion dated Nov. 26, 2021.
PCT/US2021/037635 Invitation to Pay Additional Fees dated Aug. 24, 2021.
PCT/US2021/048893 International Search Report and Written Opinion dated Dec. 7, 2021.
PCT/US2021/050413 International Search Report and Written Opinion dated Dec. 23, 2021.
Tsubokawa et al.: In vitro and clinical evaluation of optical coherence tomography for the detection of subgingival calculus and root cementum. J Oral Sci. 60(3):418-427 (2018).
U.S. Appl. No. 16/774,679 Final Office Action dated Apr. 29, 2022.
U.S. Appl. No. 17/000,175 Office Action dated Jan. 11, 2022.
U.S. Appl. No. 16/073,057 Office Action dated Jul. 31, 2019.
U.S. Appl. No. 16/486,662 Restriction Requirement dated Apr. 29, 2022.
U.S. Appl. No. 16/774,679 Final Office Action dated Jul. 21, 2021.
U.S. Appl. No. 16/774,679 Office Action dated Oct. 19, 2020.
U.S. Appl. No. 16/774,679 Office Action dated Oct. 26, 2021.
U.S. Appl. No. 17/000,175 Final Office Action dated Aug. 24, 2021.
U.S. Appl. No. 17/000,175 First Action Interview dated Jun. 4, 2021.
U.S. Appl. No. 17/000,175 First Action Interview dated Mar. 22, 2021.
U.S. Appl. No. 17/054,445 Office Action dated Feb. 18, 2022.
Visuri et al.: Shear Strength of Composite Bonded to Er:YAG Laser-prepared Dentin. J Dent Res; 75(1):599-605 (1996).
Yuan et al.: An automatic tooth preparation technique: A preliminary study; Scientific Reports|6:25281|DOI:10.1038/srep25281, pp. 1-9 (2016).
Huang et al.: Miniaturized Water-Jet Ultrasound Indentation System for Quantitative Assessment of Articular Cartilage Degeneration: A Validation Study. BioMed Research International. 13 pages (2020).
PCT/US2021/048893 International Preliminary Report on Patentability dated Mar. 16, 2023.
PCT/US2022/022550 PCT International Search Report and Written Opinion dated Aug. 16, 2022.
PCT/US2022/022550 PCT Invitation to Pay Additional Fees dated Jun. 3, 2022.
URL https://en.wikipedia.org/wiki/Smoothness, printed Sep. 11, 2023, 9 pages.

* cited by examiner

METHOD AND APPARATUS FOR CNA ANALYSIS OF TOOTH ANATOMY

CROSS-REFERENCE

This application is a continuation of International Application No. PCT/US2021/048893, filed Sep. 2, 2021, which claims the benefit of U.S. Provisional Application No. 63/074,400, filed Sep. 3, 2020, each of which are incorporated by reference in their entirety herein.

BACKGROUND

Restoration dental procedures with prosthetics are performed daily to cure a variety of oral conditions. The ability to optimize the geometries the prosthetic and the cut tooth improves the effectiveness of such procedures and reduces patient side effects.

SUMMARY

One aspect provided herein is a computer-implemented method of directing an automated dental drill (ADD) for preparation of a target tooth of a patient for a restoration with a prosthesis by a practitioner, the method comprising: receiving: a prosthesis material comprising a material property; an applied bite force; a force limit; a displacement limit; and a three-dimensional (3D) tooth model of the target tooth comprising a removal portion; determining a first 3D preparation geometry and a first 3D prosthesis geometry based on the 3D tooth model and the prosthesis material; performing a finite element analysis (FEA) to determine a first force and a first displacement based on the first 3D preparation geometry, the first 3D prosthesis geometry, the prosthesis material, and the applied bite force; if the first force is greater than the force limit or if the first displacement is greater than the displacement limit: determining a second 3D preparation geometry and a second 3D prosthesis geometry based on the first force, the first displacement, the first 3D preparation geometry, and the first 3D prosthesis geometry; and performing a finite element analysis (FEA) to determine a second force and a second displacement based on the second 3D preparation geometry, the second 3D prosthesis geometry, the prosthesis material, and the applied bite force; and if the first force is less than the force limit or if the second displacement is greater than the displacement limit: instructing the ADD to cut the target tooth based on the first 3D preparation geometry. In some embodiments, the prosthesis the restoration comprises a crown, an inlay, an onlay, a veneer, a bridge, a pontic, a core, or a direct restoration. In some embodiments, the prosthetic material comprises gold, porcelain, ceramic, multi-layer ceramic, composite resin, amalgam, lithium disilicate, zirconia, or any combination thereof. In some embodiments, the force limit is based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, or any combination thereof. In some embodiments, the force limit is based on a force required to dislodge or fracture the restoration from the target tooth during mastication, clenching, grinding, or any combination thereof. In some embodiments, the displacement limit is based on a displacement required to dislodge at least a portion of the prosthesis from the target tooth, a displacement required to displace at least a portion of the prosthesis relative to the target tooth, a fatigue displacement over a longevity period required to dislodge at least a portion of the prosthesis from the target tooth, or any combination thereof. In some embodiments, the displacement limit is based on a displacement required to dislodge the restoration from the target tooth during mastication, clenching, grinding, or any combination thereof. In some embodiments, at least one of the force limit, the first force, and the second force comprises a lingual to buccal force, a buccal to lingual force, a mesial to distal force, a distal to mesial force, an upper jaw to lower jaw force, or any other combination thereof. In some embodiments, at least one of the displacement limit, the first displacement, and the second displacement comprises a lingual to buccal displacement, a buccal to lingual displacement, a mesial to distal displacement, a distal to mesial displacement, an upper jaw to lower jaw displacement, or any other combination thereof. In some embodiments, the 3D tooth model comprises the target tooth and a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 500 microns. In some embodiments, the method further comprises receiving a treatment input comprising a preparation strength, an adhesive strength, a nerve geometry of the target tooth, a pulp geometry of the target tooth, a pulp volume of the target tooth, a decayed geometry of the target tooth, a cusp depth, a preparation height, a preparation cut angle, a surgical preparation time, a margin placement location, a margin placement tolerance, a prosthesis material, a carries volume, a crack localization and volume, a tooth defect volume, a tooth defect localization, a previous prosthesis material, an allowed range of critical dimensions of preparations, an allowed range of critical dimensions of prosthesis, a prosthesis strength, a clinician defined metrics, a dental research defined metrics, or any combination thereof. In some embodiments, the first force, the second force, or both is further determined based on the treatment input. In some embodiments, the first displacement, the second displacement, or both is further determined based on the treatment input. In some embodiments, the method further comprises receiving an anti-rotation geometry, wherein the first 3D preparation geometry, the first 3D prosthesis geometry, the second 3D preparation geometry, second first 3D prosthesis geometry, or any combination thereof comprise the anti-rotation geometry. In some embodiments, the first force, the second force, or both is further determined based on the anti-rotation geometry. In some embodiments, the first displacement, the second displacement, or both is further determined based on the anti-rotation geometry. In some embodiments, the method further comprises instructing the ADD to cut the target tooth based on the second 3D preparation geometry if the second force is less than the force limit or if the second displacement is greater than the displacement limit. In some embodiments, the first 3D preparation geometry, the first 3D prosthesis geometry, the second 3D preparation geometry, the second 3D prosthesis geometry, or any combination thereof are determined by a machine learning method.

Another aspect provided herein is a computer-implemented system comprising: a digital processing device comprising: at least one processor, an operating system configured to perform executable instructions, a memory, and a computer program including instructions executable by the digital processing device to create an application for directing an automated dental drill (ADD) for preparation of a target tooth of a patient for a restoration with a prosthesis by a practitioner, the application performing at least the following: a receiving: a prosthesis material comprising a material property; an applied bite force; a force limit; a displacement limit; and a three-dimensional (3D) tooth model of the target tooth comprising a removal portion; determining a first 3D preparation geometry and a first 3D prosthesis geometry based on the 3D tooth model and the prosthesis material; performing a finite element analysis (FEA) to determine a first force and a first displacement based on the first 3D preparation geometry, the first 3D prosthesis geometry, the prosthesis material, and the applied bite force; if the first force is greater than the force limit or if the first displacement is greater than the displacement limit: determining a second 3D preparation geometry and a second 3D prosthesis geometry based on the first force, the first displacement, the first 3D preparation geometry, and the first 3D prosthesis geometry; and performing a finite element analysis (FEA) to determine a second force and a second displacement based on the second 3D preparation geometry, the second 3D prosthesis geometry, the prosthesis material, and the applied bite force; and if the first force is less than the force limit or if the second displacement is greater than the displacement limit: instructing the ADD to cut the target tooth based on the first 3D preparation geometry.

In some embodiments, the prosthesis the restoration comprises a crown, an inlay, an onlay, a veneer, a bridge, a pontic, a core, or a direct restoration. In some embodiments, the prosthetic material comprises gold, porcelain, ceramic, multi-layer ceramic, composite resin, amalgam, lithium disilicate, zirconia, or any combination thereof. In some embodiments, the force limit is based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, or any combination thereof. In some embodiments, the force limit is based on a force required to dislodge or fracture the restoration from the target tooth during mastication, clenching, grinding, or any combination thereof. In some embodiments, the displacement limit is based on a displacement required to dislodge at least a portion of the prosthesis from the target tooth, a displacement required to displace at least a portion of the prosthesis relative to the target tooth, a fatigue displacement over a longevity period required to dislodge at least a portion of the prosthesis from the target tooth, or any combination thereof. In some embodiments, the displacement limit is based on a displacement required to dislodge the restoration from the target tooth during mastication, clenching, grinding, or any combination thereof. In some embodiments, at least one of the force limit, the first force, and the second force comprises a lingual to buccal force, a buccal to lingual force, a mesial to distal force, a distal to mesial force, an upper jaw to lower jaw force, or any other combination thereof. In some embodiments, at least one of the displacement limit, the first displacement, and the second displacement comprises a lingual to buccal displacement, a buccal to lingual displacement, a mesial to distal displacement, a distal to mesial displacement, an upper jaw to lower jaw displacement, or any other combination thereof. In some embodiments, the 3D tooth model comprises the target tooth and a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 500 microns. In some embodiments, the application further performs receiving a treatment input comprising a preparation strength, an adhesive strength, a nerve geometry of the target tooth, a pulp geometry of the target tooth, a pulp volume of the target tooth, a decayed geometry of the target tooth, a cusp depth, a preparation height, a preparation cut angle, a surgical preparation time, a margin placement location, a margin placement tolerance, a prosthesis material, a carries volume, a crack localization and volume, a tooth defect volume, a tooth defect localization, a previous prosthesis material, an allowed range of critical dimensions of preparations, an allowed range of critical dimensions of prosthesis, a prosthesis strength, a clinician defined metrics, a dental research defined metrics, or any combination thereof. In some embodiments, the first force, the second force, or both is further determined based on the treatment input. In some embodiments, the first displacement, the second displacement, or both is further determined based on the treatment input. In some embodiments, the application further performs receiving an anti-rotation geometry, wherein the first 3D preparation geometry, the first 3D prosthesis geometry, the second 3D preparation geometry, second first 3D prosthesis geometry, or any combination thereof comprise the anti-rotation geometry. In some embodiments, the first force, the second force, or both is further determined based on the anti-rotation geometry. In some embodiments, the first displacement, the second displacement, or both is further determined based on the anti-rotation geometry. In some embodiments, the application further performs instructing the ADD to cut the target tooth based on the second 3D preparation geometry if the second force is less than the force limit or if the second displacement is greater than the displacement limit. In some embodiments, the first 3D preparation geometry, the first 3D prosthesis geometry, the second 3D preparation geometry, the second 3D prosthesis geometry, or any combination thereof are determined by a machine learning method.

Another aspect provided herein is a non-transitory computer-readable storage media encoded with a computer program including instructions executable by a processor to create an application for directing an automated dental drill (ADD) for preparation of a target tooth of a patient for a restoration with a prosthesis by a practitioner, the application performing at least the following: a receiving: a prosthesis material comprising a material property; an applied bite force; a force limit; a displacement limit; and a three-dimensional (3D) tooth model of the target tooth comprising a removal portion; determining a first 3D preparation geometry and a first 3D prosthesis geometry based on the 3D tooth model and the prosthesis material; performing a finite element analysis (FEA) to determine a first force and a first displacement based on the first 3D preparation geometry, the first 3D prosthesis geometry, the prosthesis material, and the applied bite force; if the first force is greater than the force limit or if the first displacement is greater than the displacement limit: determining a second 3D preparation geometry and a second 3D prosthesis geometry based on the first force, the first displacement, the first 3D preparation geometry, and the first 3D prosthesis geometry; and performing a finite element analysis (FEA) to determine a second force and a second displacement based on the second 3D preparation geometry, the second 3D prosthesis geometry, the prosthesis material, and the applied bite force; and if the first force is less than the force limit or if the second displacement is greater than the displacement limit: instructing the ADD to cut the target tooth based on the first 3D preparation geometry.

In some embodiments, the prosthesis the restoration comprises a crown, an inlay, an onlay, a veneer, a bridge, a pontic, a core, or a direct restoration. In some embodiments, the prosthetic material comprises gold, porcelain, ceramic, multi-layer ceramic, composite resin, amalgam, lithium disilicate, zirconia, or any combination thereof. In some embodiments, the force limit is based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, or any combination thereof. In some embodiments, the force limit is based on a force required to dislodge or fracture the restoration from the target tooth during mastication, clenching, grinding, or any combination thereof. In some embodiments, the displacement limit is based on a displacement required to dislodge at least a portion of the prosthesis from the target tooth, a displacement required to displace at least a portion of the prosthesis relative to the target tooth, a fatigue displacement over a longevity period required to dislodge at least a portion of the prosthesis from the target tooth, or any combination thereof. In some embodiments, the displacement limit is based on a displacement required to dislodge the restoration from the target tooth during mastication, clenching, grinding, or any combination thereof. In some embodiments, at least one of the force limit, the first force, and the second force comprises a lingual to buccal force, a buccal to lingual force, a mesial to distal force, a distal to mesial force, an upper jaw to lower jaw force, or any other combination thereof. In some embodiments, at least one of the displacement limit, the first displacement, and the second displacement comprises a lingual to buccal displacement, a buccal to lingual displacement, a mesial to distal displacement, a distal to mesial displacement, an upper jaw to lower jaw displacement, or any other combination thereof. In some embodiments, the 3D tooth model comprises the target tooth and a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 500 microns. In some embodiments, the application further performs receiving a treatment input comprising a preparation strength, an adhesive strength, a nerve geometry of the target tooth, a pulp geometry of the target tooth, a pulp volume of the target tooth, a decayed geometry of the target tooth, a cusp depth, a preparation height, a preparation cut angle, a surgical preparation time, a margin placement location, a margin placement tolerance, a prosthesis material, a carries volume, a crack localization and volume, a tooth defect volume, a tooth defect localization, a previous prosthesis material, an allowed range of critical dimensions of preparations, an allowed range of critical dimensions of prosthesis, a prosthesis strength, a clinician defined metrics, a dental research defined metrics, or any combination thereof. In some embodiments, the first force, the second force, or both is further determined based on the treatment input. In some embodiments, the first displacement, the second displacement, or both is further determined based on the treatment input. In some embodiments, the application further performs receiving an anti-rotation geometry, wherein the first 3D preparation geometry, the first 3D prosthesis geometry, the second 3D preparation geometry, second first 3D prosthesis geometry, or any combination thereof comprise the anti-rotation geometry. In some embodiments, the first force, the second force, or both is further determined based on the anti-rotation geometry. In some embodiments, the first displacement, the second displacement, or both is further determined based on the anti-rotation geometry. In some embodiments, the application further performs instructing the ADD to cut the target tooth based on the second 3D preparation geometry if the second force is less than the force limit or if the second displacement is greater than the displacement limit. In some embodiments, the first 3D preparation geometry, the first 3D prosthesis geometry, the second 3D preparation geometry, the second 3D prosthesis geometry, or any combination thereof are determined by a machine learning method.

One aspect provided herein is a computer-implemented method of directing an automated dental drill (ADD) for preparation of a target tooth of a patient for restoration (using a prosthesis) by a practitioner, the method a comprising: receiving a material property for the prosthesis; receiving expected maximum applied bite forces; receiving a limits on resulting forces and displacements; receiving a three-dimensional (3D) tooth model including the target tooth, wherein at least a portion of the 3D model comprises a removal portion; determining an initial 3D preparation geometry and an initial 3D prosthesis geometry based on the 3D tooth model and the prosthetic material; performing a finite element analysis (FEA) to determine resulting forces and displacements on the preparation and the prosthesis based on the initial 3D preparation geometry, the initial 3D prosthetic geometry, the prosthetic material and the applied forces; iteratively determining an updated 3D preparation geometry and an updated 3D prosthetic geometry based on the calculated forces and displacements, the initial 3D preparation geometry, and the initial 3D prosthetic geometry until all limits on resulting forces and displacements are satisfied; and instructing the ADD to cut the target tooth based on the updated 3D preparation geometry.

In some embodiments, the restoration comprises a crown, an inlay, an onlay, a veneer, a bridge, a pontic, a core, or a direct restoration. In some embodiments, the prosthetic material comprises gold, porcelain, ceramic, multi-layer ceramic, composite resin, amalgam, lithium disilicate, zirconia, or other dental prosthetic material. In some embodiments, the force and displacement limits are based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, a force required to fracture at least a portion of the prosthesis or any combination thereof. In some embodiments, the force and displacement limits are based on the force required to dislodge the prosthesis from the target tooth during mastication, clenching, grinding, or any combination thereof. In some embodiments, the force and displacement limits are based on the force required to fracture at least a portion of the prosthesis during mastication, clenching, grinding, or any combination thereof. In some embodiments, the updated 3D preparation geometry, the updated 3D prosthetic geometry, or both are only determined if the force and displacement limits are below a predefined threshold. In some embodiments, the 3D tooth model further comprises a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 100 microns. In some embodiments, the FEA is performed with an analysis mesh size of about 100 micron to about 500 microns. In some embodiments, the initial 3D preparation geometry, the updated 3D geometry, or both, comprise at least the removal portion. In some embodiments, the force and displacement limits comprise a limit for lingual to buccal loading, buccal to lingual loading, mesial to distal loading, distal to mesial loading, an upper jaw to lower jaw loading, a lower jaw to upper jaw loading, or any other combination thereof. In some embodiments, the method further comprises receiving a treatment input comprising a preparation strength, an adhesive strength, a nerve geometry of the target tooth, a pulp geometry of the target tooth, a pulp volume of the target tooth, a decayed geometry of the target tooth, a cusp height, a preparation height, a preparation cut angle, a surgical preparation time, a margin placement location, a margin placement tolerance, a prosthetic material, a carries volume, a crack localization and volume, a tooth defect volume and localization, a previous prosthetic material, an allowed range of critical dimensions of preparations, an allowed range of critical dimensions of prosthetics, a prosthetic strength, a clinician defined metrics, a dental research defined metrics, or any combination thereof. In some embodiments, the force and displacement limits are further determined based on the treatment input. In some embodiments, the method further includes receiving an anti-rotation geometry, anti-displacement geometry, or both, wherein the initial 3D preparation geometry, the initial 3D prosthetic geometry, or both include the anti-rotation geometry, anti-displacement geometry, or both. In some embodiments, the force and displacement limits are further based on the anti-rotation geometry, the anti-displacement geometry, or both. In some embodiments, the updated 3D preparation geometry, the updated 3D prosthetic geometry, or both, comprise an updated anti rotation geometry.

Another aspect provided herein is a computer-implemented system comprising: a digital processing device comprising: at least one processor, an operating system configured to perform executable instructions, a memory, and a computer program including instructions executable by the digital processing device to create an application for directing an automated dental drill (ADD) to prepare of one or more teeth of a patient and a restoration by a practitioner, the application comprising: a module receiving a prosthetic material properties for the restoration; a module receiving a three-dimensional (3D) tooth model of the target tooth, wherein at least a portion of the 3D model comprises a removal portion; a module determining an initial 3D preparation geometry and an initial 3D prosthetic geometry based on the 3D tooth model and the prosthetic material; a module performing a finite element analysis (FEA) to determine forces and displacements applied to the preparation and the prosthesis based on the initial 3D preparation geometry, the initial 3D prosthetic geometry, and the prosthetic material; a module iteratively determining an updated 3D preparation geometry and an updated 3D prosthetic geometry based on the calculated forces and displacements, the initial 3D preparation geometry, and the initial 3D prosthetic geometry; and a module instructing the ADD to cut the target tooth based on the updated 3D preparation geometry.

In some embodiments, the restoration comprises an inlay, an onlay, a veneer, a bridge, a pontic, a core, or a direct restoration. In some embodiments, the material property comprises a restoration compressive strength, a restoration shear strength, a restoration density, or any combination thereof. In some embodiments, the force and displacement limits are based on a force required to dislodge at least a portion of the restoration from the target tooth, a force required to displace at least a portion of the restoration relative to the target tooth, a fatigue force over a longevity period required to dislodge at least a portion of the restoration from the target tooth, or any combination thereof. In some embodiments, the force and displacement limits are based on a force required to dislodge the restoration from the target tooth during mastication, clenching, grinding, or any combination thereof. In some embodiments, the updated 3D preparation geometry, the updated 3D prosthetic geometry, or both are only determined if the force and displacement limits are below a predefined threshold. In some embodiments, the 3D tooth model further comprises a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 100 microns. In some embodiments, the initial 3D preparation geometry, the updated 3D geometry, or both, comprise at least the removal portion. In some embodiments, the force and displacement limits comprises a limits for lingual to buccal loading, buccal to lingual loading, mesial to distal loading, distal to mesial loading, an upper jaw to lower jaw loading, or any other combination thereof. In some embodiments, the application further comprises a module receiving a treatment input comprising a preparation strength, an adhesive strength, a nerve geometry of the target tooth, a pulp geometry of the target tooth, a pulp volume of the target tooth, a decayed geometry of the target tooth, a cusp height, a preparation height, a preparation cut angle, a surgical preparation time, a margin placement location, a margin placement tolerance, a prosthetic material, a carries volume, a crack localization and volume, a tooth defect volume and localization, a previous prosthetic material, an allowed range of critical dimensions of preparations, an allowed range of critical dimensions of prosthetics, a prosthetic strength, a clinician defined metrics, a dental research defined metrics, or any combination thereof. In some embodiments, limits on forces and displacements are further determined based on the treatment input. In some embodiments, the application further comprises receiving an anti-rotation geometry, wherein the initial 3D preparation geometry, the initial 3D prosthetic geometry, or both comprise the anti-rotation geometry. In some embodiments, the force and displacement limits are further based on the anti-rotation geometry. In some embodiments, the updated 3D preparation geometry, the updated 3D prosthetic geometry, or both, comprise an updated anti rotation geometry.

A non-transitory computer-readable storage media encoded with a computer program including instructions executable by a processor to create an application for directing an automated dental drill (ADD) to prepare of one or more teeth of a patient and a restoration by a practitioner, the application comprising: a module receiving a prosthetic material property of the restoration; a module receiving a three-dimensional (3D) tooth model of the target tooth, wherein at least a portion of the 3D model comprises a removal portion; a module determining an initial 3D preparation geometry and an initial 3D prosthetic geometry based on the 3D tooth model and the prosthetic material; a module performing a finite element analysis (FEA) to determine forces and displacements applied to the preparation and the prosthesis based on the initial 3D preparation geometry, the initial 3D prosthetic geometry, and the prosthetic material; a module determining an updated 3D preparation geometry and an updated 3D prosthetic geometry based on the bite force factor of safety, the initial 3D preparation geometry, and the initial 3D prosthetic geometry; and a module instructing the ADD to cut the target tooth based on the updated 3D preparation geometry, wherein the restoration comprises a crown, an inlay, an onlay, a veneer, a bridge, a pontic, a core, or a direct restoration. In some embodiments, the material property comprises a restoration compressive strength, a restoration shear strength, a restoration density, or any combination thereof.

In some embodiments, the restoration comprises a crown, an inlay, an onlay, a veneer, a bridge, a pontic, a core, or a direct restoration. In some embodiments, the material property comprises a restoration compressive strength, a restoration shear strength, a restoration density, or any combination thereof. In some embodiments, the force and displacement limits are based on a force required to dislodge at least a portion of the restoration from the target tooth, a force required to displace at least a portion of the restoration relative to the target tooth, a fatigue force over a longevity period required to dislodge at least a portion of the restoration from the target tooth, or any combination thereof. In some embodiments, the force and displacement limits are based on a force required to dislodge the restoration from the target tooth during mastication, clenching, grinding, or any combination thereof. In some embodiments, the updated 3D preparation geometry, the updated 3D prosthetic geometry, or both are only determined if the force and displacement limits are below a predefined threshold. In some embodiments, the 3D tooth model further comprises a tooth adjacent to the target tooth, a tooth opposite the target tooth, or both. In some embodiments, the FEA comprises finite volume analysis, finite difference analysis, computational numerical analysis, or any combination thereof. In some embodiments, the FEA is performed with an analysis mesh size of about 1 micron to about 100 microns. In some embodiments, the initial 3D preparation geometry, the updated 3D geometry, or both, comprise at least the removal portion. In some embodiments, the force and displacement limits comprise a limit for lingual to buccal loading, buccal to lingual loading, mesial to distal loading, distal to mesial loading, an upper jaw to lower jaw loading, a lower jaw to upper jaw loading, or any other combination thereof. In some embodiments, the application further comprises a module receiving a treatment input comprising a preparation strength, an adhesive strength, a nerve geometry of the target tooth, a pulp geometry of the target tooth, a pulp volume of the target tooth, a decayed geometry of the target tooth, a cusp height, a preparation height, a preparation cut angle, a surgical preparation time, a margin placement location, a margin placement tolerance, a prosthetic material, a carries volume, a crack localization and volume, a tooth defect volume and localization, a previous prosthetic material, an allowed range of critical dimensions of preparations, an allowed range of critical dimensions of prosthetics, a prosthetic strength, a clinician defined metrics, a dental research defined metrics, or any combination thereof. In some embodiments, force and displacement limits are further determined based on the treatment input. In some embodiments, the application further comprises receiving an anti-rotation geometry, wherein the initial 3D preparation geometry, the initial 3D prosthetic geometry, or both comprise the anti-rotation geometry. In some embodiments, the force and displacement limits are further based on the anti-rotation geometry. In some embodiments, the updated 3D prepara-tion geometry, the updated 3D prosthetic geometry, or both, comprise an updated anti rotation geometry.

Another aspect provided herein is a computer-implemented method of directing an automated dental drill (ADD) for preparation of a target tooth of a patient for restoration (using a prosthesis) by a practitioner, the method a comprising: receiving a material property for the prosthesis; receiving expected maximum applied bite forces; receiving a limits on resulting forces and displacements; receiving a three-dimensional (3D) tooth model including the target tooth, wherein at least a portion of the 3D model comprises a removal portion; employing AI techniques such as Machine Learning or a pre-trained Neural Network to determine the 3D preparation geometry and the 3D prosthetic geometry; and instructing the ADD to cut the target tooth based on the updated 3D preparation geometry.

Another aspect provided herein is a computer-implemented method of directing an automated dental drill (ADD) for preparation of a target tooth of a patient for restoration (using a prosthesis) by a practitioner, the method a comprising: receiving a material property for the prosthesis; receiving expected maximum applied bite forces; receiving a limits on resulting forces and displacements; receiving a three-dimensional (3D) tooth model including the target tooth, wherein at least a portion of the 3D model comprises a removal portion; determining an initial 3D preparation geometry and an initial 3D prosthesis geometry based on the 3D tooth model and the prosthetic material; performing a finite element analysis (FEA) to determine resulting forces and displacements on the preparation and the prosthesis based on the initial 3D preparation geometry, the initial 3D prosthetic geometry, the prosthetic material and the applied forces; iteratively determining an updated 3D preparation geometry and an updated 3D prosthetic geometry employing AI techniques such as Machine Learning or a pre-trained Neural Network based on the calculated forces and displacements, the initial or updated 3D preparation geometry, and the initial or updated 3D prosthetic geometry until all limits on resulting forces and displacements are satisfied; and instructing the ADD to cut the target tooth based on the updated 3D preparation geometry.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Provided herein are a computer-implemented method, a computer-implemented system, and a non-transitory computer-readable storage media for directing an automated dental drill (ADD) for preparation of a target tooth of a patient under the control of a practitioner. In some embodiments, computer-implemented system comprising: a digital processing device comprising: at least one processor, an operating system configured to perform executable instructions, a memory, and a computer program including instructions executable by the digital processing device to create an application. In some embodiments, the non-transitory computer-readable storage media is encoded with a computer program including instructions executable by a processor to create an application for directing an automated dental drill (ADD) to prepare of one or more teeth of a patient under the control of a practitioner.

Figure 3:
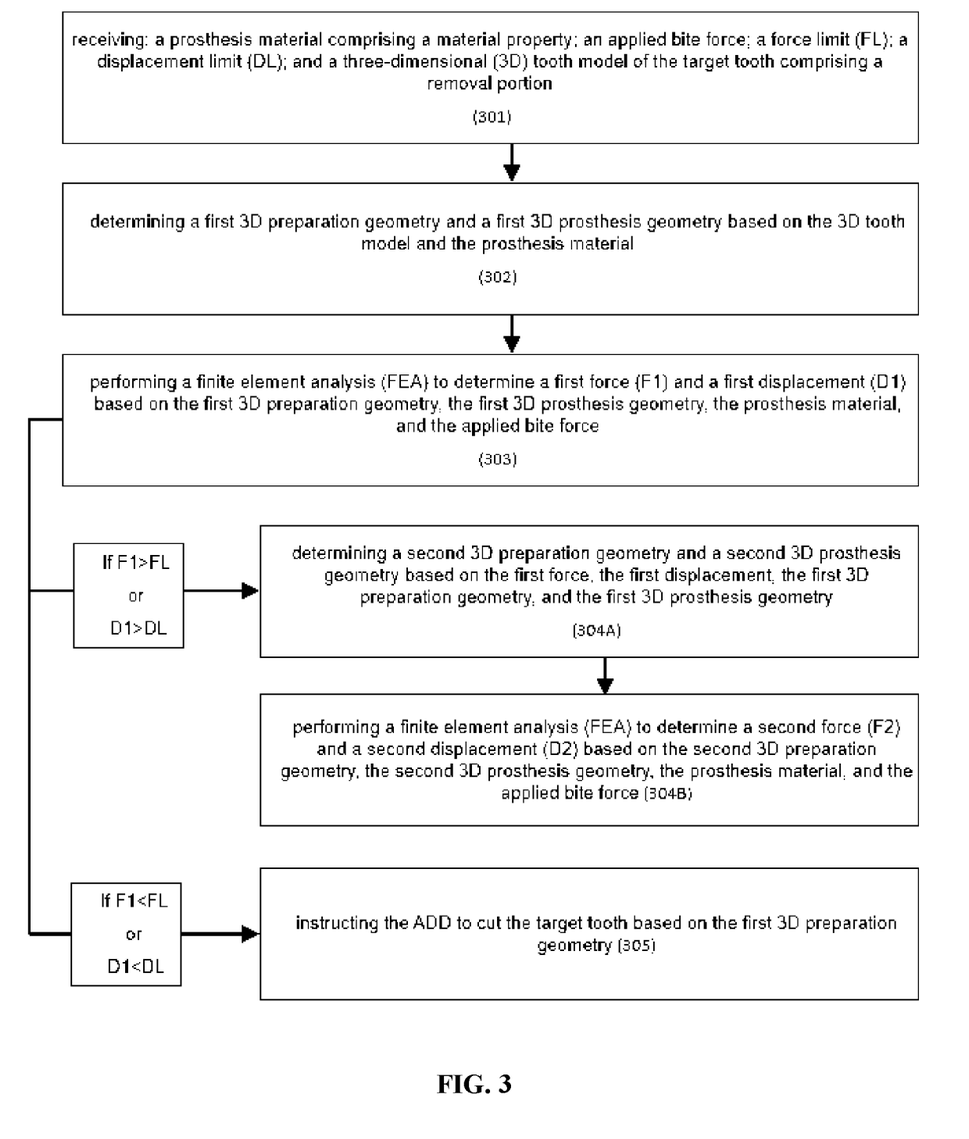
FIG. 3 shows an exemplary method of directing an automated dental drill (ADD) for preparation of one or more teeth of a patient and a crown by a practitioner, per one or more embodiments herein.

In some embodiments, per FIG. 3, the method and applications herein perform and/or comprise receiving: a prosthesis material comprising a material property; an applied bite force; a force limit; a displacement limit; and a three-dimensional (3D) tooth model of the target tooth comprising a removal portion 301; determining a first 3D preparation geometry and a first 3D prosthesis geometry based on the 3D tooth model and the prosthesis material 302; performing a finite element analysis (FEA) to determine a first force and a first displacement based on the first 3D preparation geometry, the first 3D prosthesis geometry, the prosthesis material, and the applied bite force 303; if the first force is greater than the force limit or if the first displacement is greater than the displacement limit: determining a second 3D preparation geometry and a second 3D prosthesis geometry based on the first force, the first displacement, the first 3D preparation geometry, and the first 3D prosthesis geometry 304A; and performing a finite element analysis (FEA) to determine a second force and a second displacement based on the second 3D preparation geometry, the second 3D prosthesis geometry, the prosthesis material, and the applied bite force 304B; and if the first force is less than the force limit or if the second displacement is greater than the displacement limit: instructing the ADD to cut the target tooth based on the first 3D preparation geometry 305.

In some embodiments, the restoration is a direct prosthesis, an indirect prosthesis, or both. In some embodiments, the restoration comprises a crown, an inlay, an onlay, a veneer, a bridge, a pontic, a core, or a direct restoration. In some embodiments, the pontic comprises a one-tooth pontic, a two-tooth pontic, a three-tooth pontic, or a four-tooth pontic. In some embodiments, the material property comprises a restoration compressive strength, a restoration shear strength, a restoration density, or any combination thereof. In some embodiments, the prosthesis the restoration comprises a crown, an inlay, an onlay, a veneer, a bridge, a pontic, a core, or a direct restoration. In some embodiments, the prosthetic material comprises gold, porcelain, ceramic, multi-layer ceramic, composite resin, amalgam, lithium disilicate, zirconia, or any combination thereof.

In some embodiments, the method further comprises determining a second force and a second displacement based on the second 3D preparation geometry, the second 3D prosthesis geometry, the prosthesis material, and the applied bite force; if the second force is greater than the force limit or if the second displacement is greater than the displacement limit: determining a third 3D preparation geometry and a third 3D prosthesis geometry based on the second force, the second displacement, the second 3D preparation geometry, and the second 3D prosthesis geometry; and performing a finite element analysis (FEA) to determine a third force and a third displacement based on the third 3D preparation geometry, the third 3D prosthesis geometry, the prosthesis material, and the applied bite force; and if the second force is less than the force limit or if the third displacement is greater than the displacement limit: instructing the ADD to cut the target tooth based on the second 3D preparation geometry.

In some embodiments, the method further comprises receiving a treatment input comprising a preparation strength, an adhesive strength, a nerve geometry of the target tooth, a pulp geometry of the target tooth, a pulp volume of the target tooth, a decayed geometry of the target tooth, a cusp depth, a preparation height, a preparation cut angle, a surgical preparation time, a margin placement location, a margin placement tolerance, a prosthesis material, a carries volume, a crack localization and volume, a tooth defect volume, a tooth defect localization, a previous prosthesis material, an allowed range of critical dimensions of preparations, an allowed range of critical dimensions of prosthesis, a prosthesis strength, a clinician defined metrics, a dental research defined metrics, or any combination thereof. In some embodiments, the first force, the second force, or both is further determined based on the treatment input. In some embodiments, the first displacement, the second displacement, or both is further determined based on the treatment input. In some embodiments, the method further comprises receiving an anti-rotation geometry, wherein the first 3D preparation geometry, the first 3D prosthesis geometry, the second 3D preparation geometry, second first 3D prosthesis geometry, or any combination thereof comprise the anti-rotation geometry. In some embodiments, the first force, the second force, or both is further determined based on the anti-rotation geometry. In some embodiments, the first displacement, the second displacement, or both is further determined based on the anti-rotation geometry. In some embodiments, the method further comprises instructing the ADD to cut the target tooth based on the second 3D preparation geometry if the second force is less than the force limit or if the second displacement is greater than the displacement limit. In some embodiments, the first 3D preparation geometry, the first 3D prosthesis geometry, the second 3D preparation geometry, the second 3D prosthesis geometry, or any combination thereof are determined by a machine learning method.

In some embodiments, the automated dental drill (ADD) is automatic, semi-automatic, or fully automatic. In some embodiments, the ADD is at least partially autonomous. In some embodiments, the ADD is at least partially robotically controlled. In some embodiments, the ADD is at least partially human controlled and/or directed.

3D Models

Figure 1:
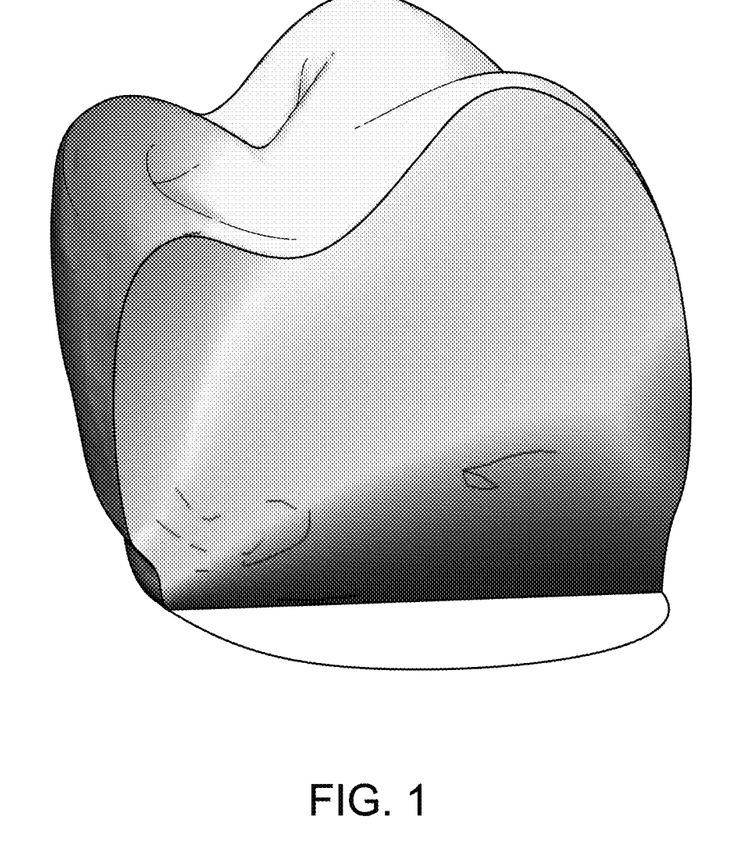
FIG. 1 shows a cross section of a first exemplary initial 3D preparation geometry model, wherein dark areas correspond to a higher bite force three-dimensional factor, per one or more embodiments herein.
Figure 2:
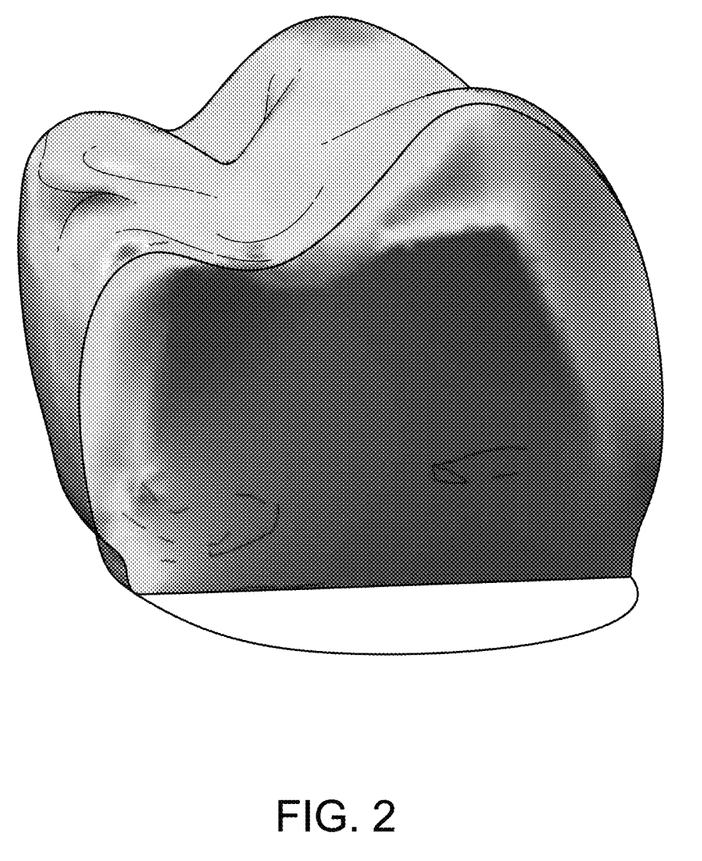
FIG. 2 shows a cross section of a second exemplary initial 3D preparation geometry model, wherein dark areas correspond to a higher bite force three-dimensional factor, per one or more embodiments herein.

FIGS. 1 and 2 show cross sections of an exemplary initial 3D preparation geometry model. In some embodiments, as shown dark areas correspond to a higher bite force three-dimensional factor.

In some embodiments, the 3D model is an X-ray 3D model, an Optical coherence tomography (OCT) 3D model, a computed tomography (CT) 3D model, an ultrasound 3D model, a tomographic 3D model, or any combination thereof. In some embodiments, the 3D model is received by an X-ray, an OCT, a CT, an ultrasound 3D model, or any combination thereof.

In some embodiments, at least a portion of the 3D model comprises a removal portion. In some embodiments, the initial 3D preparation geometry, the updated 3D geometry, or both, comprise at least the removal portion. In some embodiments, the initial 3D preparation geometry and the initial 3D prosthetic geometry are determined based on the 3D tooth model and/or the prosthetic material. In some embodiments, the updated 3D preparation geometry and the updated 3D prosthetic geometry are based on the bite force factor of safety, the initial 3D preparation geometry, the initial 3D prosthetic geometry, or any combination thereof. In some embodiments, the 3D tooth model further comprises a tooth adjacent to the target tooth, a tooth opposite the target tooth, or both.

Finite Element Analysis

In some embodiments, the FEA comprises finite volume analysis, finite difference analysis, computational numerical analysis, or any combination thereof. In some embodiments, the FEA is performed with an analysis mesh size of about 1 micron to about 500 microns. In some embodiments, the FEA is performed with an analysis mesh size of about 1 micron to about 10 microns, about 1 micron to about 50 microns, about 1 micron to about 100 microns, about 1 micron to about 150 microns, about 1 micron to about 200 microns, about 1 micron to about 250 microns, about 1 micron to about 300 microns, about 1 micron to about 350 microns, about 1 micron to about 400 microns, about 1 micron to about 450 microns, about 1 micron to about 500 microns, about 10 microns to about 50 microns, about 10 microns to about 100 microns, about 10 microns to about 150 microns, about 10 microns to about 200 microns, about 10 microns to about 250 microns, about 10 microns to about 300 microns, about 10 microns to about 350 microns, about 10 microns to about 400 microns, about 10 microns to about 450 microns, about 10 microns to about 500 microns, about 50 microns to about 100 microns, about 50 microns to about 150 microns, about 50 microns to about 200 microns, about 50 microns to about 250 microns, about 50 microns to about 300 microns, about 50 microns to about 350 microns, about 50 microns to about 400 microns, about 50 microns to about 450 microns, about 50 microns to about 500 microns, about 100 microns to about 150 microns, about 100 microns to about 200 microns, about 100 microns to about 250 microns, about 100 microns to about 300 microns, about 100 microns to about 350 microns, about 100 microns to about 400 microns, about 100 microns to about 450 microns, about 100 microns to about 500 microns, about 150 microns to about 200 microns, about 150 microns to about 250 microns, about 150 microns to about 300 microns, about 150 microns to about 350 microns, about 150 microns to about 400 microns, about 150 microns to about 450 microns, about 150 microns to about 500 microns, about 200 microns to about 250 microns, about 200 microns to about 300 microns, about 200 microns to about 350 microns, about 200 microns to about 400 microns, about 200 microns to about 450 microns, about 200 microns to about 500 microns, about 250 microns to about 300 microns, about 250 microns to about 350 microns, about 250 microns to about 400 microns, about 250 microns to about 450 microns, about 250 microns to about 500 microns, about 300 microns to about 350 microns, about 300 microns to about 400 microns, about 300 microns to about 450 microns, about 300 microns to about 500 microns, about 350 microns to about 400 microns, about 350 microns to about 450 microns, about 350 microns to about 500 microns, about 400 microns to about 450 microns, about 400 microns to about 500 microns, or about 450 microns to about 500 microns, including increments therein. In some embodiments, the FEA is performed with an analysis mesh size of about 1 micron, about 10 microns, about 50 microns, about 100 microns, about 150 microns, about 200 microns, about 250 microns, about 300 microns, about 350 microns, about 400 microns, about 450 microns, or about 500 microns. In some embodiments, the FEA is performed with an analysis mesh size of at least about 1 micron, about 10 microns, about 50 microns, about 100 microns, about 150 microns, about 200 microns, about 250 microns, about 300 microns, about 350 microns, about 400 microns, or about 450 microns. In some embodiments, the FEA is performed with an analysis mesh size of at most about 10 microns, about 50 microns, about 100 microns, about 150 microns, about 200 microns, about 250 microns, about 300 microns, about 350 microns, about 400 microns, about 450 microns, or about 500 microns.

Limits on Forces and Displacements

In some embodiments, the force limit is based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, or any combination thereof. In some embodiments, the force limit is based on a force required to dislodge or fracture the restoration from the target tooth during mastication, clenching, grinding, or any combination thereof. In some embodiments, the displacement limit is based on a displacement required to dislodge at least a portion of the prosthesis from the target tooth, a displacement required to displace at least a portion of the prosthesis relative to the target tooth, a fatigue displacement over a longevity period required to dislodge at least a portion of the prosthesis from the target tooth, or any combination thereof. In some embodiments, the displacement limit is based on a displacement required to dislodge the restoration from the target tooth during mastication, clenching, grinding, or any combination thereof. In some embodiments, at least one of the force limit, the first force, and the second force comprises a lingual to buccal force, a buccal to lingual force, a mesial to distal force, a distal to mesial force, an upper jaw to lower jaw force, or any other combination thereof. In some embodiments, at least one of the displacement limit, the first displacement, and the second displacement comprises a lingual to buccal displacement, a buccal to lingual displacement, a mesial to distal displacement, a distal to mesial displacement, an upper jaw to lower jaw displacement, or any other combination thereof. In some embodiments, the 3D tooth model comprises the target tooth and a tooth adjacent to the target tooth, a tooth opposite the target tooth, or both.

In some embodiments, the force limit is about 1 N to about 10 N. In some embodiments, the force limit is about 1 N to abut 2 N, about 1 N to abut 3 N, about 1 N to abut 4 N, about 1 N to abut 5 N, about 1 N to abut 6 N, about 1 N to abut 7 N, about 1 N to abut 8 N, about 1 N to abut 9 N, about 1 N to about 10 N, abut 2 N to abut 3 N, abut 2 N to abut 4 N, abut 2 N to abut 5 N, abut 2 N to abut 6 N, abut 2 N to abut 7 N, abut 2 N to abut 8 N, abut 2 N to abut 9 N, abut 2 N to about 10 N, abut 3 N to abut 4 N, abut 3 N to abut 5 N, abut 3 N to abut 6 N, abut 3 N to abut 7 N, abut 3 N to abut 8 N, abut 3 N to abut 9 N, abut 3 N to about 10 N, abut 4 N to abut 5 N, abut 4 N to abut 6 N, abut 4 N to abut 7 N, abut 4 N to abut 8 N, abut 4 N to abut 9 N, abut 4 N to about 10 N, abut 5 N to abut 6 N, abut 5 N to abut 7 N, abut 5 N to abut 8 N, abut 5 N to abut 9 N, abut 5 N to about 10 N, abut 6 N to abut 7 N, abut 6 N to abut 8 N, abut 6 N to abut 9 N, abut 6 N to about 10 N, abut 7 N to abut 8 N, abut 7 N to abut 9 N, abut 7 N to about 10 N, abut 8 N to abut 9 N, abut 8 N to about 10 N, or abut 9 N to about 10 N, including increments therein. In some embodiments, the force limit is about 1 N, abut 2 N, abut 3 N, abut 4 N, abut 5 N, abut 6 N, abut 7 N, abut 8 N, abut 9 N, or about 10 N. In some embodiments, the force limit is at least about 1 N, abut 2 N, abut 3 N, abut 4 N, abut 5 N, abut 6 N, abut 7 N, abut 8 N, or abut 9 N. In some embodiments, the force limit is at most abut 2 N, abut 3 N, abut 4 N, abut 5 N, abut 6 N, abut 7 N, abut 8 N, abut 9 N, or about 10 N.

In some embodiments, the displacement limit is about 1 micron to about 500 microns. In some embodiments, the displacement limit is about 1 micron to abut 25 microns, about 1 micron to about 50 microns, about 1 micron to about 100 microns, about 1 micron to about 150 microns, about 1 micron to about 200 microns, about 1 micron to about 250 microns, about 1 micron to about 300 microns, about 1 micron to about 350 microns, about 1 micron to about 400 microns, about 1 micron to about 450 microns, about 1 micron to about 500 microns, abut 25 microns to about 50 microns, abut 25 microns to about 100 microns, abut 25 microns to about 150 microns, abut 25 microns to about 200 microns, abut 25 microns to about 250 microns, abut 25 microns to about 300 microns, abut 25 microns to about 350 microns, abut 25 microns to about 400 microns, abut 25 microns to about 450 microns, abut 25 microns to about 500 microns, about 50 microns to about 100 microns, about 50 microns to about 150 microns, about 50 microns to about 200 microns, about 50 microns to about 250 microns, about 50 microns to about 300 microns, about 50 microns to about 350 microns, about 50 microns to about 400 microns, about 50 microns to about 450 microns, about 50 microns to about 500 microns, about 100 microns to about 150 microns, about 100 microns to about 200 microns, about 100 microns to about 250 microns, about 100 microns to about 300 microns, about 100 microns to about 350 microns, about 100 microns to about 400 microns, about 100 microns to about 450 microns, about 100 microns to about 500 microns, about 150 microns to about 200 microns, about 150 microns to about 250 microns, about 150 microns to about 300 microns, about 150 microns to about 350 microns, about 150 microns to about 400 microns, about 150 microns to about 450 microns, about 150 microns to about 500 microns, about 200 microns to about 250 microns, about 200 microns to about 300 microns, about 200 microns to about 350 microns, about 200 microns to about 400 microns, about 200 microns to about 450 microns, about 200 microns to about 500 microns, about 250 microns to about 300 microns, about 250 microns to about 350 microns, about 250 microns to about 400 microns, about 250 microns to about 450 microns, about 250 microns to about 500 microns, about 300 microns to about 350 microns, about 300 microns to about 400 microns, about 300 microns to about 450 microns, about 300 microns to about 500 microns, about 350 microns to about 400 microns, about 350 microns to about 450 microns, about 350 microns to about 500 microns, about 400 microns to about 450 microns, about 400 microns to about 500 microns, or about 450 microns to about 500 microns, including increments therein. In some embodiments, the displacement limit is about 1 micron, abut 25 microns, about 50 microns, about 100 microns, about 150 microns, about 200 microns, about 250 microns, about 300 microns, about 350 microns, about 400 microns, about 450 microns, or about 500 microns. In some embodiments, the displacement limit is at least about 1 micron, abut 25 microns, about 50 microns, about 100 microns, about 150 microns, about 200 microns, about 250 microns, about 300 microns, about 350 microns, about 400 microns, or about 450 microns. In some embodiments, the displacement limit is at most abut 25 microns, about 50 microns, about 100 microns, about 150 microns, about 200 microns, about 250 microns, about 300 microns, about 350 microns, about 400 microns, about 450 microns, or about 500 microns.

In some embodiments, the limits on forces and displacements are determined based on the initial 3D preparation geometry, the initial 3D prosthetic geometry, the prosthetic material, or any combination thereof. In some embodiments, the limits on forces and displacements are based on a force required to dislodge at least a portion of the restoration from the target tooth, a force required to displace at least a portion of the restoration relative to the target tooth, a fatigue force over a longevity period required to dislodge at least a portion of the restoration from the target tooth, or any combination thereof. In some embodiments, the limits on forces and displacements are based on a force required to dislodge the restoration from the target tooth during mastication, clenching, grinding, or any combination thereof. In some embodiments, the updated 3D preparation geometry, the updated 3D prosthetic geometry, or both are only determined if limits on forces and displacements are satisfied. In some embodiments, the methods and/or applications herein instruct the ADD to cut the target tooth based on the 3D preparation geometry if the limits on forces and displacements are satisfied.

In some embodiments, the methods and applications herein further perform a second FEA to determine an updated bite force factor of safety based on the updated 3D preparation geometry, the updated 3D prosthetic geometry, and the prosthetic material, if the bite force factor of safety is above the predefined threshold factor of safety. In some embodiments, the methods and applications herein further determine a second updated 3D preparation geometry and a second updated 3D prosthetic geometry based on the updated bite force factor of safety, the updated 3D preparation geometry, and the updated 3D prosthetic geometry if the bite force factor of safety is above the predefined threshold factor of safety. In some embodiments, this iterative approach of calculating a factor of safety, improving the preparation and/or prosthetic geometry, and recalculating the factor of safety ensures greater durability and strength of the restoration procedure.

In some embodiments, the iterative 3D restoration design is optimized to maximize the strength of the prosthetic, the resistance and retention form of the tooth, the longevity of the restoration, the volume of the updated 3D prosthetic geometry, the strength of the tooth, the resistance of the tooth to fracture, or any combination thereof. In some embodiments, the iterative 3D restoration design is optimized to minimize tooth failure, prosthetic displacement, or both.

In some embodiments, the limits on forces and displacements comprise a limits on forces and displacements for lingual to buccal loading, buccal to lingual loading, mesial to distal loading, distal to mesial loading, an upper jaw to lower jaw loading, a lower jaw to upper jaw loading, or any other combination thereof. In some embodiments, the limits on forces and displacements comprise limits for symmetric loading. In some embodiments, the limits on forces and displacements comprise limits for asymmetric loading. In some embodiments, the limits on forces and displacements are further determined based on the treatment input. In some embodiments, the limits on forces and displacements are further based on the anti-rotation geometry, anti-displacement geometry, or both.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Computing System

Figure 4:
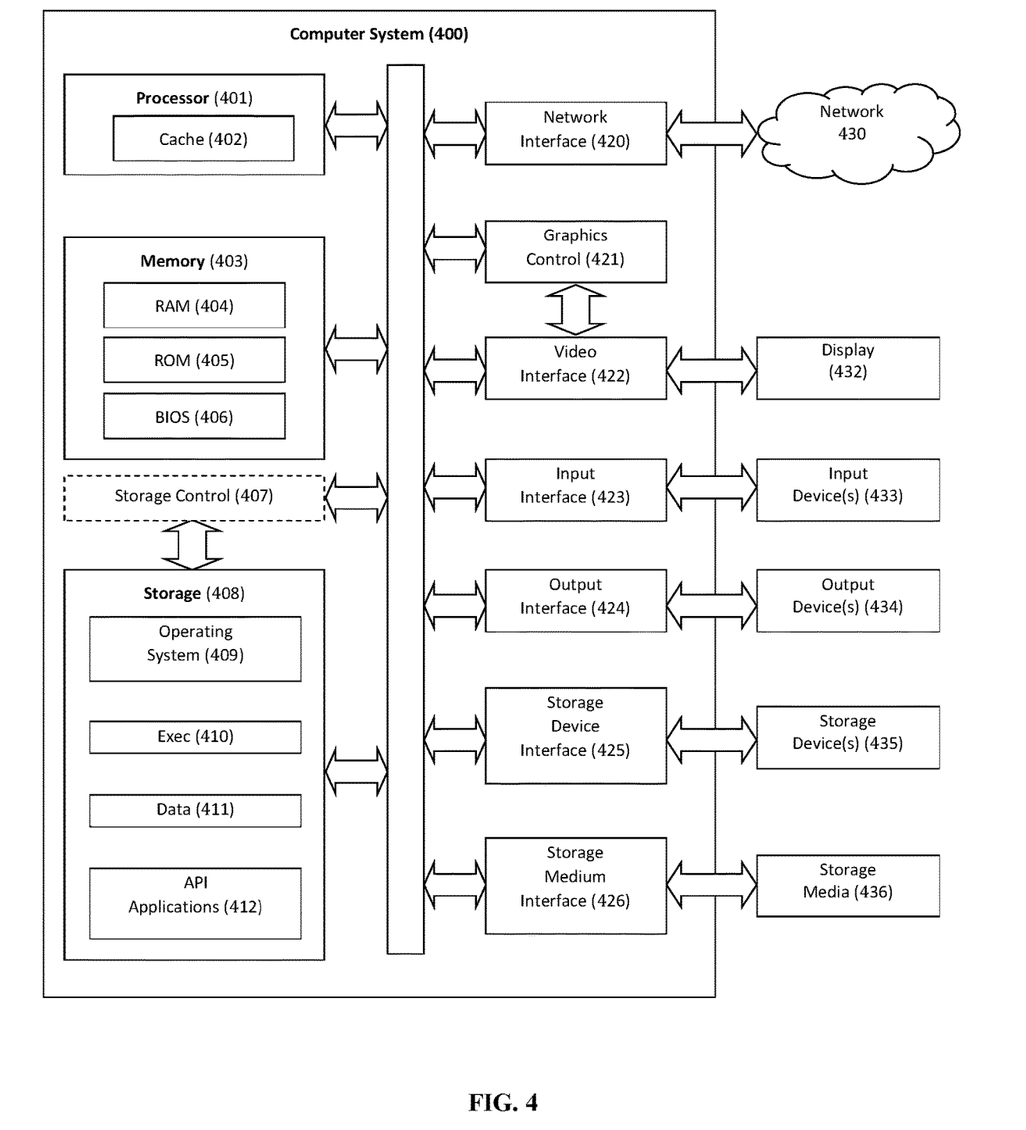
FIG. 4 shows a non-limiting example of a computing device; in this case, a device with one or more processors, memory, storage, and a network interface, per one or more embodiments herein.

Referring to FIG. 4, a block diagram is shown depicting an exemplary machine that includes a computer system 400 (e.g., a processing or computing system) within which a set of instructions can execute for causing a device to perform or execute any one or more of the aspects and/or methodologies for static code scheduling of the present disclosure. The components in FIG. 4 are examples only and do not limit the scope of use or functionality of any hardware, software, embedded logic component, or a combination of two or more such components implementing particular embodiments.

Computer system 400 may include one or more processors 401, a memory 403, and a storage 408 that communicate with each other, and with other components, via a bus 440. The bus 440 may also link a display 432, one or more input devices 433 (which may, for example, include a keypad, a keyboard, a mouse, a stylus, etc.), one or more output devices 434, one or more storage devices 435, and various tangible storage media 436. All of these elements may interface directly or via one or more interfaces or adaptors to the bus 440. For instance, the various tangible storage media 436 can interface with the bus 440 via storage medium interface 426. Computer system 400 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 400 includes one or more processor(s) 401 (e.g., central processing units (CPUs) or general purpose graphics processing units (GPGPUs)) that carry out functions. Processor(s) 401 optionally contains a cache memory unit 402 for temporary local storage of instructions, data, or computer addresses. Processor(s) 401 are configured to assist in execution of computer readable instructions. Computer system 400 may provide functionality for the components depicted in FIG. 4 as a result of the processor(s) 401 executing non-transitory, processor-executable instructions embodied in one or more tangible computer-readable storage media, such as memory 403, storage 408, storage devices 435, and/or storage medium 436. The computer-readable media may store software that implements particular embodiments, and processor(s) 401 may execute the software. Memory 403 may read the software from one or more other computer-readable media (such as mass storage device(s) 435, 436) or from one or more other sources through a suitable interface, such as network interface 420. The software may cause processor(s) 401 to carry out one or more processes or one or more steps of one or more processes described or illustrated herein. Carrying out such processes or steps may include defining data structures stored in memory 403 and modifying the data structures as directed by the software.

The memory 403 may include various components (e.g., machine readable media) including, but not limited to, a random access memory component (e.g., RAM 404) (e.g., static RAM (SRAM), dynamic RAM (DRAM), ferroelectric random access memory (FRAM), phase-change random access memory (PRAM), etc.), a read-only memory component (e.g., ROM 405), and any combinations thereof. ROM 405 may act to communicate data and instructions unidirectionally to processor(s) 401, and RAM 404 may act to communicate data and instructions bidirectionally with processor(s) 401. ROM 405 and RAM 404 may include any suitable tangible computer-readable media described below. In one example, a basic input/output system 406 (BIOS), including basic routines that help to transfer information between elements within computer system 400, such as during start-up, may be stored in the memory 403.

Fixed storage 408 is connected bidirectionally to processor(s) 401, optionally through storage control unit 407. Fixed storage 408 provides additional data storage capacity and may also include any suitable tangible computer-readable media described herein. Storage 408 may be used to store operating system 409, executable(s) 410, data 411, applications 412 (application programs), and the like. Storage 408 can also include an optical disk drive, a solid-state memory device (e.g., flash-based systems), or a combination of any of the above. Information in storage 408 may, in appropriate cases, be incorporated as virtual memory in memory 403.

In one example, storage device(s) 435 may be removably interfaced with computer system 400 (e.g., via an external port connector (not shown)) via a storage device interface 425. Particularly, storage device(s) 435 and an associated machine-readable medium may provide non-volatile and/or volatile storage of machine-readable instructions, data structures, program modules, and/or other data for the computer system 400. In one example, software may reside, completely or partially, within a machine-readable medium on storage device(s) 435. In another example, software may reside, completely or partially, within processor(s) 401.

Bus 440 connects a wide variety of subsystems. Herein, reference to a bus may encompass one or more digital signal lines serving a common function, where appropriate. Bus 440 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 400 may also include an input device 433. In one example, a user of computer system 400 may enter commands and/or other information into computer system 400 via input device(s) 433. Examples of an input device(s) 433 include, but are not limited to, an alphanumeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 433 may be interfaced to bus 440 via any of a variety of input interfaces 423 (e.g., input interface 423) including, but not limited to, serial, parallel, game port, USB, FIREWIRE, THUNDERBOLT, or any combination of the above.

In particular embodiments, when computer system 400 is connected to network 430, computer system 400 may communicate with other devices, specifically mobile devices and enterprise systems, distributed computing systems, cloud storage systems, cloud computing systems, and the like, connected to network 430. Communications to and from computer system 400 may be sent through network interface 420. For example, network interface 420 may receive incoming communications (such as requests or responses from other devices) in the form of one or more packets (such as Internet Protocol (IP) packets) from network 430, and computer system 400 may store the incoming communications in memory 403 for processing. Computer system 400 may similarly store outgoing communications (such as requests or responses to other devices) in the form of one or more packets in memory 403 and communicated to network 430 from network interface 420. Processor(s) 401 may access these communication packets stored in memory 403 for processing.

Examples of the network interface 420 include, but are not limited to, a network interface card, a modem, and any combination thereof. Examples of a network 430 or network segment 430 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 430, may employ a wired and/or a wireless mode of communication. In general, any network topology may be used.

Information and data can be displayed through a display 432. Examples of a display 432 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 432 can interface to the processor(s) 401, memory 403, and fixed storage 408, as well as other devices, such as input device(s) 433, via the bus 440. The display 432 is linked to the bus 440 via a video interface 422, and transport of data between the display 432 and the bus 440 can be controlled via the graphics control 421. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 432, computer system 400 may include one or more other peripheral output devices 434 including, but not limited to, an audio speaker, a printer, a storage device, and any combinations thereof. Such peripheral output devices may be connected to the bus 440 via an output interface 424. Examples of an output interface 424 include, but are not limited to, a serial port, a parallel connection, a USB port, a FIREWIRE port, a THUNDERBOLT port, and any combinations thereof.

In addition or as an alternative, computer system 400 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecastt, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Machine Learning

In some embodiments, machine learning algorithms are utilized to determine wherein the first 3D preparation geometry, the first 3D prosthesis geometry, the second 3D preparation geometry, the second 3D prosthesis geometry, or any combination thereof.

In some embodiments, the machine learning algorithms herein employ one or more forms of labels including but not limited to human annotated labels and semi-supervised labels. In some embodiments, the machine learning algorithm utilizes regression modeling, wherein relationships between predictor variables and dependent variables are determined and weighted. The human annotated labels can be provided by a hand-crafted heuristic. The semi-supervised labels can employ a XGBoost, a neural network, or both.

In some embodiments, the first 3D preparation geometry, the first 3D prosthesis geometry, the second 3D preparation geometry, the second 3D prosthesis geometry, or any combination thereof is determined using a distant supervision method. The distant supervision method can create a large training set seeded by a small hand-annotated training set. The distant supervision method can comprise positive-unlabeled learning with the training set as the 'positive' class. The distant supervision method can employ a logistic regression model, a recurrent neural network, or both. The recurrent neural network can be advantageous for Natural Language Processing (NLP) machine learning.

Examples of machine learning algorithms can include a support vector machine (SVM), a naïve Bayes classification, a random forest, a neural network, deep learning, or other supervised learning algorithm or unsupervised learning algorithm for classification and regression. The machine learning algorithms can be trained using one or more training datasets.

In some embodiments, a machine learning algorithm is used to select catalogue images and recommend project scope. A non-limiting example of a multi-variate linear regression model algorithm is seen below: probability=$A_0$+ $A_1(X_1)$+$A_2(X_2)$+$A_3(X_3)$+$A_4(X_4)$+$A_5(X_5)$+$A_6(X_6)$+ $A_7(X_7)$ . . . wherein $A_i$ ($A_1$, $A_2$, $A_3$, $A_4$, $A_5$, $A_6$, $A_7$, . . . ) are "weights" or coefficients found during the regression modeling; and $X_i$ ($X_1$, $X_2$, $X_3$, $X_4$, $X_5$, $X_6$, $X_7$, . . . ) are data collected from a user. Any number of $A_i$ and $X_i$ variable can be included in the model.

What is claimed is:

1. A computer-implemented method of directing an automated dental drill (ADD) for preparation of a target tooth of a patient for a restoration with a prosthesis by a practitioner, the method comprising:
   (a) a computing device with one or more processors receiving:
      (i) a prosthesis material comprising a material property;
      (ii) an applied bite force;
      (iii) a force limit;
      (iv) a displacement limit; and
      (v) a three-dimensional (3D) tooth model of the target tooth comprising a three-dimensional (3D) model of the target tooth in an unmodified state and a three-dimensional (3D) model of a removal portion;
   (b) determining a first 3D preparation geometry and a first 3D prosthesis geometry based on the 3D tooth model and the prosthesis material;
   (c) performing a finite element analysis (FEA) to determine a first force and a first displacement based on the first 3D preparation geometry, the first 3D prosthesis geometry, the prosthesis material, and the applied bite force;
   (d) if the first force is greater than the force limit or if the first displacement is greater than the displacement limit:
      (i) determining a second 3D preparation geometry and a second 3D prosthesis geometry based on the first force, the first displacement, the first 3D preparation geometry, and the first 3D prosthesis geometry; and
      (ii) performing a finite element analysis (FEA) to determine a second force and a second displacement based on the second 3D preparation geometry, the second 3D prosthesis geometry, the prosthesis material, and the applied bite force; and
   (e) if the first force is less than the force limit or if the second displacement is greater than the displacement limit:
      (i) instructing the ADD to cut the target tooth based on the first 3D preparation geometry.

2. The method of claim 1, wherein the prosthesis for the restoration comprises a crown, an inlay, an onlay, a veneer, a bridge, a pontic, a core, or a direct restoration.

3. The method of claim 1, wherein the prosthetic material comprises gold, porcelain, ceramic, multi-layer ceramic, composite resin, amalgam, lithium disilicate, zirconia, or any combination thereof.

4. The method of claim 1, wherein the force limit is based on a force required to dislodge at least a portion of the prosthesis from the target tooth, a force required to displace at least a portion of the prosthesis relative to the target tooth, a fatigue force over a longevity period required to dislodge at least a portion of the prosthesis from the target tooth, or any combination thereof.

5. The method of claim 1, wherein the force limit is based on a force required to dislodge or fracture the restoration from the target tooth during mastication, clenching, grinding, or any combination thereof.

6. The method of claim 1, wherein the displacement limit is based on a displacement required to dislodge at least a portion of the prosthesis from the target tooth, a displacement required to displace at least a portion of the prosthesis relative to the target tooth, a fatigue displacement over a longevity period required to dislodge at least a portion of the prosthesis from the target tooth, or any combination thereof.

7. The method of claim 1, wherein the displacement limit is based on a displacement required to dislodge the restoration from the target tooth during mastication, clenching, grinding, or any combination thereof.

8. The method of claim 1, wherein at least one of the force limit, the first force, and the second force comprises a lingual to buccal force, a buccal to lingual force, a mesial to distal force, a distal to mesial force, an upper jaw to lower jaw force, or any combination thereof.

9. The method of claim 1, wherein at least one of the displacement limit, the first displacement, and the second displacement comprises a lingual to buccal displacement, a buccal to lingual displacement, a mesial to distal displacement, a distal to mesial displacement, an upper jaw to lower jaw displacement, or any combination thereof.

10. The method of claim 1, wherein the 3D tooth model comprises the target tooth and a tooth adjacent to the target tooth, a tooth opposite the target tooth, or both.

11. The method of claim 1, wherein the FEA comprises finite volume analysis, finite difference analysis, computational numerical analysis, or any combination thereof.

12. The method of claim 1, wherein the FEA is performed with an analysis mesh size of about 1 micron to about 500 microns.

13. The method of claim 1, further comprising receiving a treatment input comprising a preparation strength, an adhesive strength, a nerve geometry of the target tooth, a pulp geometry of the target tooth, a pulp volume of the target tooth, a decayed geometry of the target tooth, a cusp depth, a preparation height, a preparation cut angle, a surgical preparation time, a margin placement location, a margin placement tolerance, a prosthesis material, a carries volume, a crack localization and volume, a tooth defect volume, a tooth defect localization, a previous prosthesis material, an allowed range of critical dimensions of preparations, an allowed range of critical dimensions of prosthesis, a prosthesis strength, a clinician defined metrics, a dental research defined metrics, or any combination thereof.

14. The method of claim 13, wherein (c) performing the finite element analysis (FEA) to determine the first force is also based on the treatment input, or wherein (d)(ii) performing the finite element analysis (FEA) to determine the second force is also based on the treatment input, or both.

15. The method of claim 14, wherein (c) performing the finite element analysis (FEA) to determine the first displacement is also based on the treatment input, or wherein (d)(ii) performing the finite element analysis (FEA) to determine the second displacement is also based on the treatment input, or both.

16. The method of claim 1, further comprising receiving an anti-rotation geometry, wherein the first 3D preparation geometry, the first 3D prosthesis geometry, the second 3D preparation geometry, second first 3D prosthesis geometry, or any combination thereof comprise the anti-rotation geometry.

17. The method of claim 16, wherein (c) performing the finite element analysis (FEA) to determine the first force is also based on the anti-rotation geometry, or wherein (d)(ii) performing the finite element analysis (FEA) to determine the the second force is also determined based on the anti-rotation geometry, or both.

18. The method of claim 17, wherein (c) performing the finite element analysis (FEA) to determine the first displacement is also based on the anti-rotation geometry, or wherein (d)(ii) performing the finite element analysis (FEA) to determine the second displacement is also determined based on the anti-rotation geometry, or both.

19. The method of claim 1, further comprising (f) if the second force is less than the force limit: (i) instructing the ADD to cut the target tooth based on the second 3D preparation geometry.

20. The method of claim 1, wherein (b) determining the first 3D preparation geometry and the first 3D prosthesis geometry comprises utilizing a machine learning algorithm, or wherein (d)(i) determining the second 3D preparation geometry and the second 3D prosthesis geometry comprises utilizing a machine learning algorithm, or both.

* * * * *